(12) United States Patent
Ebara et al.

(10) Patent No.: US 12,357,845 B2
(45) Date of Patent: Jul. 15, 2025

(54) SUPERCONDUCTIVE ELECTROMAGNET, PARTICLE ACCELERATOR, AND PARTICLE BEAM THERAPY APPARATUS

(71) Applicant: SUMITOMO HEAVY INDUSTRIES, LTD., Tokyo (JP)

(72) Inventors: Yuta Ebara, Kanagawa (JP); Jyun Yoshida, Kanagawa (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 726 days.

(21) Appl. No.: 17/707,362

(22) Filed: Mar. 29, 2022

(65) Prior Publication Data

US 2022/0314024 A1     Oct. 6, 2022

(30) Foreign Application Priority Data

Mar. 30, 2021    (JP) ................................ 2021-057183

(51) Int. Cl.
*A61N 5/10*      (2006.01)
*H01F 6/06*      (2006.01)

(52) U.S. Cl.
CPC ............. *A61N 5/1048* (2013.01); *H01F 6/06* (2013.01); *A61N 2005/1087* (2013.01); *A61N 2005/1089* (2013.01)

(58) Field of Classification Search
CPC .......... A61N 5/1048; A61N 2005/1087; A61N 2005/1089; H01F 6/06
See application file for complete search history.

(56) References Cited

U.S. PATENT DOCUMENTS

| | | | |
|---|---|---|---|
| 2009/0219121 A1 | 9/2009 | Atkins et al. | |
| 2013/0009571 A1 | 1/2013 | Antaya | |
| 2015/0340141 A1* | 11/2015 | Yoshida | H01F 6/06 505/211 |
| 2017/0330739 A1 | 11/2017 | Hosaka | |
| 2019/0024950 A1 | 1/2019 | Ebara et al. | |

FOREIGN PATENT DOCUMENTS

| | | |
|---|---|---|
| CN | 105288866 A | 2/2016 |
| CN | 107078020 A | 8/2017 |
| CN | 109074932 A | 12/2018 |
| JP | 2020-021901 A | 2/2020 |
| TW | 201304619 A | 1/2013 |

OTHER PUBLICATIONS

Office Action issued in Taiwan Application No. 11220216520, dated Mar. 6, 2023.

* cited by examiner

*Primary Examiner* — Nicole M Ippolito
(74) *Attorney, Agent, or Firm* — Michael Best & Friedrich LLP

(57) ABSTRACT

In a case where a start current value is higher than a target current value, a control unit performs a control to lower a current value from the start current value to the target current value. In addition, in a case where the start current value is equal to or lower than the target current value, the control unit controls to raise the current value from the start current value to the format current value higher than the target current value, and then lower the current value to the target current value. In this manner, regardless of the value of the predetermined current value before the current value is changed, the current value reaches the target current value in a descending manner. As a result, the coil magnetization magnetic field when the target current value is reached can be kept in the same state.

7 Claims, 11 Drawing Sheets

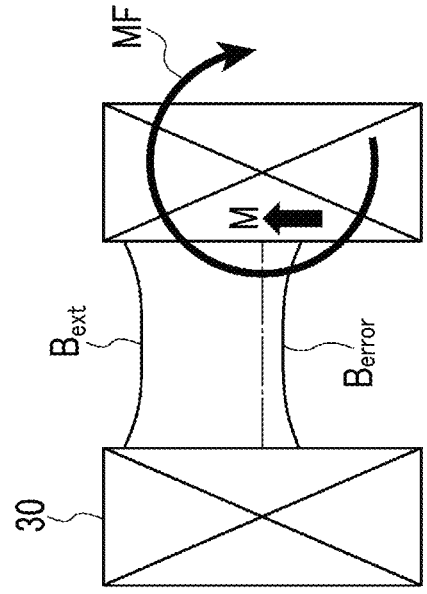
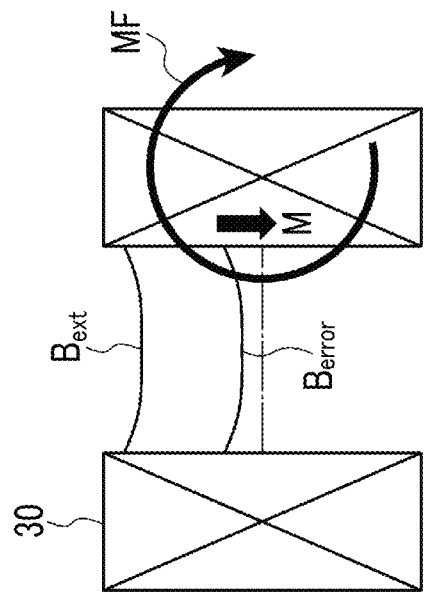

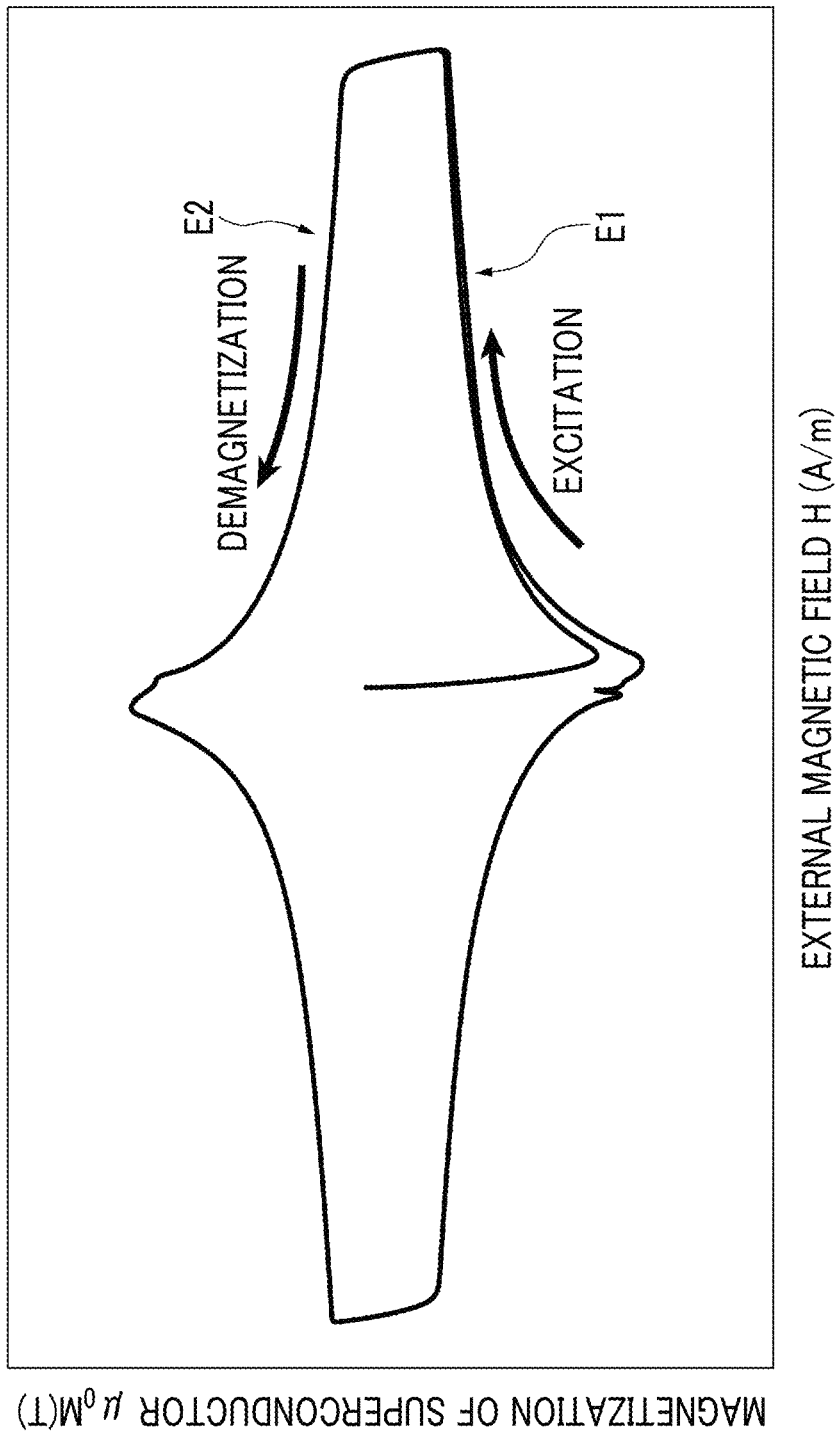

SUPERCONDUCTIVE ELECTROMAGNET, PARTICLE ACCELERATOR, AND PARTICLE BEAM THERAPY APPARATUS

RELATED APPLICATIONS

The content of Japanese Patent Application No. 2021-057183, on the basis of which priority benefits are claimed in an accompanying application data sheet, is in its entirety incorporated herein by reference.

BACKGROUND

Technical Field

Certain embodiment of the present invention relates to a superconductive electromagnet, a particle accelerator, and a particle beam therapy apparatus.

Description of Related Art

A superconductive electromagnet is provided with a coil and a vacuum chamber. The coil is an annular member formed by winding a superconductive wire. The coil is disposed so as to surround a magnetic pole. The superconductive electromagnet forms a strong magnetic field by creating a vacuum state inside the vacuum chamber and then flowing a current through the coil in a superconductivity state by a cooler. As a device using such a superconductive electromagnet, for example, a particle accelerator as described in the related art is known.

SUMMARY

According to an aspect of the present invention, there is provided a superconductive electromagnet that generates a magnetic field by flowing a current through a coil, the electromagnet including a control unit that controls a current value of the coil, in which the control unit performs a control to lower the current value from a predetermined current value of the coil to a target current value in a case where the predetermined current value is higher than the target current value, and performs a control to raise the current value from the predetermined current value to a format current value higher than the target current value and then lower the current value to the target current value in a case where the predetermined current value is equal to or lower than the target current value.

According to another aspect of the present invention, there is provided a superconductive electromagnet that generates a magnetic field by flowing a current through a coil, the electromagnet including a control unit that controls a current value of the coil, in which the control unit performs a control to raise the current value from a predetermined current value of the coil to a target current value in a case where the predetermined current value is lower than the target current value, and performs a control to lower the current value from the predetermined current value to a format current value lower than the target current value and then raise the current value to the target current value in a case where the predetermined current value is equal to or higher than the target current value.

According to still another aspect of the present invention, there is provided a superconductive electromagnet that generates a magnetic field by flowing a current through a coil, the electromagnet including a control unit that controls a current value of the coil, in which the control unit estimates a magnetic field due to magnetization of the coil generated by a change of the current value, and causes a current value deviated from a target current value by the magnetic field due to the magnetization of the coil to flow through the coil.

According to still another aspect of the present invention, there is provided a particle accelerator including the above-described superconductive electromagnet and accelerates a particle to generate a particle beam.

According to still another aspect of the present invention, there is provided a particle beam therapy apparatus including the above-described particle accelerator, and performing treatment using a particle beam generated by the particle accelerator.

BRIEF DESCRIPTION OF THE DRAWINGS

FIGS. 3A and 3B are schematic diagrams for describing a coil magnetization magnetic field.

FIG. 4 is a graph of a magnetization curve illustrating a relationship between a magnetic field formed by a coil by energization and the coil magnetization magnetic field.

DETAILED DESCRIPTION

Figure 1:
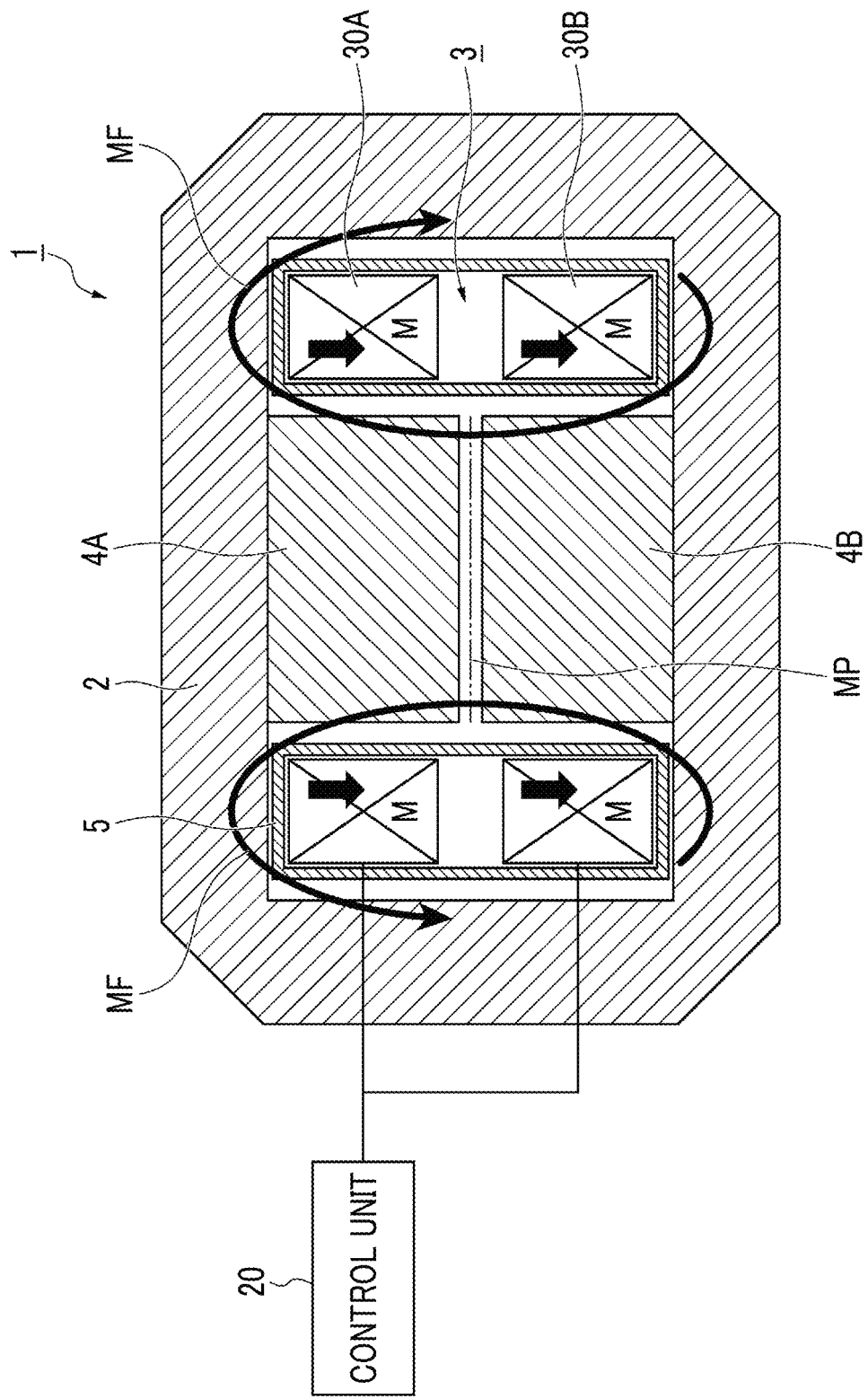
FIG. 1 is a schematic cross-sectional view illustrating a particle accelerator mounted with a superconductive electromagnet according to the present embodiment.

Here, when a current flows through a coil, a magnetic field is formed around the coil. In this case, in the coil, a superconductor inside the coil is magnetized (coil magnetization magnetic field) using the magnetic field formed by energization as an external magnetic field. Such a coil magnetization magnetic field affects the magnetic field formed around the coil. Such a coil magnetization magnetic field may cause a problem such as a phase deviation of an acceleration voltage frequency in the above-described particle accelerator or the like. Therefore, there has been a demand for a superconductive electromagnet that can reduce the influence of the coil magnetization magnetic field.

Therefore, it is desirable to provide a superconductive electromagnet, a particle accelerator, and a particle beam therapy apparatus capable of reducing an influence of a coil magnetization magnetic field.

In the superconductive electromagnet, in a case where the current value of the coil is changed from the predetermined current value to the target current value, there is a difference in the coil magnetization magnetic field even though the current value is the same as in a case where the target current value is reached by lowering the current value and in a case where the target current value is reached by raising the current value. On the other hand, in a case where the predetermined current value of the coil is higher than the target current value, the control unit performs the control to lower the current value from the predetermined current value to the target current value. In this case, the current value reaches the target current value in a descending manner. In addition, in a case where the predetermined current value is equal to or lower than the target current value, the control unit performs the control to raise the current value from the predetermined current value to the format current value higher than the target current value and then lower the current value to the target current value. In this case, the current value reaches the target current value in a descending manner. In this manner, the current value reaches the target current value in a descending manner regardless of the value of the predetermined current value before the current value is changed. As a result, the coil magnetization magnetic field when the target current value is reached can be kept in the same state regardless of the predetermined current value before the current value is changed. Therefore, the influence of the coil magnetization magnetic field can be reduced.

In a case where the predetermined current value of the coil is lower than the target current value, the control unit controls to raise the current value from the predetermined current value to the target current value. In this case, the current value reaches the target current value in an ascending manner. In addition, in a case where the predetermined current value is equal to or higher than the target current value, the control unit performs the control to lower the current value from the predetermined current value to the format current value lower than the target current value and then raise the current value to the target current value. In this case, the current value reaches the target current value in an ascending manner. In this manner, the current value reaches the target current value in an ascending manner regardless of the value of the predetermined current value before the current value is changed. As a result, the coil magnetization magnetic field when the target current value is reached can be kept in the same state regardless of the predetermined current value before the current value is changed. Therefore, the influence of the coil magnetization magnetic field can be reduced.

The control unit estimates the magnetic field due to the magnetization of the coil generated by the change in the current value, and causes the current value deviated from the target current value by the magnetic field due to the magnetization of the coil to flow through the coil. In this case, the control unit can control the current value flowing through the coil by feedforward controlling the coil magnetization magnetic field in advance when changing from the predetermined current value to the target current value. As a result, a magnetic field is formed around the coil in an aspect in which the coil magnetization magnetic field is reduced. Therefore, the influence of the coil magnetization magnetic field can be reduced.

The control unit may keep the current value of the coil constant at the format current value for a predetermined time. In this case, sufficient time can be secured for the coil magnetization magnetic field to change.

In an initial sweep control of the current value, the control unit may perform the control to raise the current value to the maximum value that is obtainable in second and subsequent sweep controls. The value of the coil magnetization magnetic field can transition over the entire magnetization curve related to the initial magnetization process by the initial sweep control. As a result, in the second and subsequent sweep controls, it is possible to suppress the change in the value of the coil magnetization magnetic field along the magnetization curve related to the initial magnetization process.

According to these particle accelerators and particle beam therapy apparatus, the same action or effect as those of the above-described superconductive electromagnets can be obtained.

Hereinafter, various embodiments will be described in detail with reference to the drawings. In each drawing, the same or corresponding portions are designated by the same reference numerals, and duplicated description will be omitted.

Figure 2:
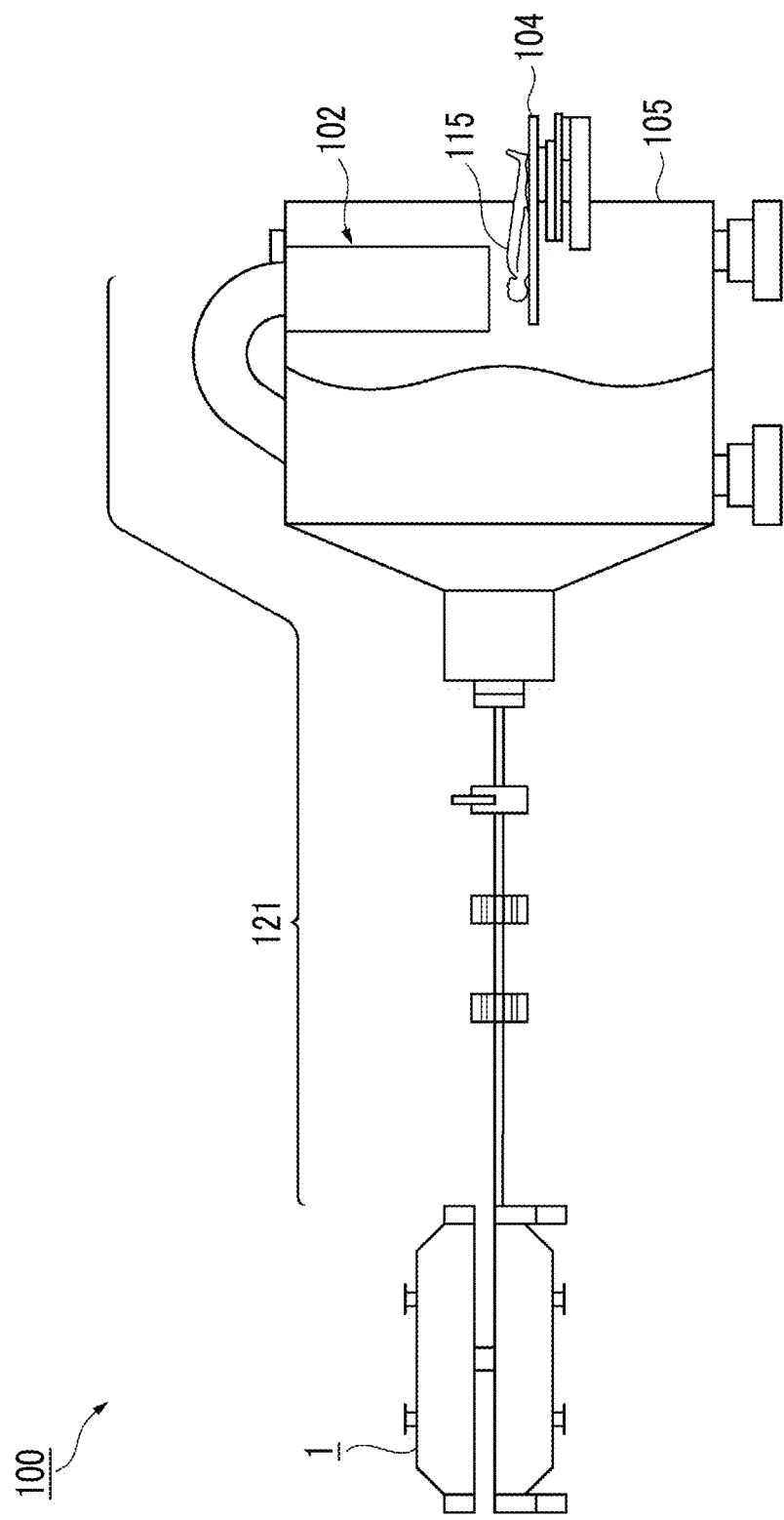
FIG. 2 is a schematic cross-sectional view illustrating a particle beam therapy apparatus mounted with the superconductive electromagnet according to the present embodiment.

FIG. 1 is a schematic cross-sectional view illustrating a particle accelerator mounted with a superconductive electromagnet according to the present embodiment. The particle accelerator 1 illustrated in FIG. 1 is a cyclotron used to accelerate a charged particle supplied from an ion source (not illustrated) to generate a charged particle beam and exit the charged particle beam, for example, in a neutron capture therapy system that performs a cancer treatment using boron neutron capture therapy (BNCT). Examples of the charged particles include protons, heavy particles (heavy ions), electrons, and the like. In addition, the particle accelerator 1 can also be used as a cyclotron for PET, a cyclotron for RI production, a cyclotron for nuclear experiments, and the like. In addition, the particle accelerator 1 may be adopted in a particle beam therapy apparatus 100 as illustrated in FIG. 2. The particle beam therapy apparatus 100 illustrated in FIG. 2 is provided with a particle accelerator 1, a transportation line 121, an irradiator 102, and a rotary gantry 105. The irradiator 102 exits a particle beam generated by the particle accelerator and is transported by the transportation line 121. A patient on a treatment table 104 is irradiated with the irradiator 102. The irradiator 102 is attached to the rotary gantry 105, and the irradiation position in the rotation direction is adjusted by the rotary gantry 105. The particle accelerator 1 is not limited to the cyclotron, and may be a synchrocyclotron.

Returning to FIG. 1, the particle accelerator 1 is provided with a yoke 2, a superconductive electromagnet 3, a pair of magnetic poles 4A and 4B, and a vacuum chamber 5.

The yoke 2 supports the superconductive electromagnet 3, the pair of magnetic poles 4A and 4B, the vacuum chamber 5, and the like. The yoke 2 is a hollow disk-shaped block, and the pair of magnetic poles 4A and 4B forming a magnetic field necessary for accelerating the charged particle are provided inside the yoke 2. The magnetic poles 4A and 4B have a circular shape in a plan view, and are disposed so as to face each other with a median plane MP (acceleration plane in which the charged particle accelerates) interposed therebetween. The superconductive electromagnet 3 is disposed around the magnetic poles 4A and 4B.

The superconductive electromagnet 3 is provided with a pair of coils 30A and 30B, the vacuum chamber 5, and a control unit 20. Each of the coils 30A and 30B is annular and is formed by winding a superconductive wire. Each of the coils 30A and 30B are disposed so as to surround the magnetic poles 4A and 4B. The material of the superconductive wire is not particularly limited, and NbTi, Nb$_3$Sn, MgB$_2$, Bi-based superconductivity (Bi2223, Bi2212, and the like), rare earth-based superconductivity, iron-based superconductivity, and the like may be adopted.

The vacuum chamber 5 is a container that accommodates the coils 30A and 30B in a vacuum state. The vacuum chamber 5 and a cryocooler (not illustrated) constitute a cryostat capable of cooling the coils 30A and 30B until the coils are in a superconductivity state. As the cryocooler, for example, a Gifford-McMahon (GM) cooler can be used. The type of the cryocooler is not limited to the GM cryocooler, and may be another cryocooler such as a Stirling cryocooler.

In the particle accelerator 1, a strong magnetic field is formed by creating a vacuum state inside the vacuum chamber 5 and then flowing a current through the coil of the superconductive electromagnet 3 in a superconductivity state by a cooler. The charged particle supplied from the ion source (not illustrated) is accelerated by the influence of the magnetic field on the median plane MP in a space between the magnetic poles 4A and 4B, and is exited as a charged particle beam.

The control unit 20 is a device that controls the current values of the coils 30A and 30B. Here, in order to describe the control contents of the control unit 20, the coil magnetization magnetic field of the coil 30 will be described with reference to FIGS. 3A and 3B. In a case where the coils 30A and 30B are not particularly distinguished, the coils are referred to as a "coil 30". When a current flows through the coil 30, a magnetic field MF is formed around the coil 30. In this case, in the coil 30, a superconductor inside the coil 30 is magnetized (coil magnetization magnetic field) using the magnetic field MF as an external magnetic field. Such a coil magnetization magnetic field affects the magnetic field formed around the coil 30. In FIGS. 3A and 3B, "B$_{error}$" indicates a coil magnetization magnetic field. "B$_{ext}$" is the magnetic field formed by the coil 30 by energization excluding B$_{error}$. Here, as illustrated in FIGS. 3A and 3B, the values and behaviors of the coil magnetization magnetic fields are different from each other due to the influence of the mutual inductance M between the case where the coil 30 is excited by increasing the current value and the case where the coil 30 is demagnetized by decreasing the current value. Specifically, FIG. 4 is a graph of a magnetization curve illustrating a relationship between the magnetic field formed by the coil 30 by energization and the coil magnetization magnetic field. The horizontal axis of FIG. 4 illustrates an external magnetic field, and the vertical axis illustrates the magnetization of the superconductor. Even in a case where the relationship between the current value and the coil magnetization magnetic field is drawn by regarding the current value as the horizontal axis, the shape is substantially the same as that in FIG. 4. Therefore, the horizontal axis of FIG. 4 may be regarded as the current value. In addition, the value on the vertical axis may be simply referred to as a "value of the coil magnetization magnetic field". As illustrated in FIG. 4, when the current value of the coil 30 is increased in a region on the positive side, the value of the coil magnetization magnetic field transitions along a magnetization curve E1 on the negative side of the graph. When the current value of the coil 30 is reduced in the region on the positive side, the value of the coil magnetization magnetic field transitions along a magnetization curve E2 on the positive side of the graph. In this manner, the coil magnetization magnetic field due to the influence of the coil magnetization magnetic field depends on a current sweep pattern.

Figure 5:
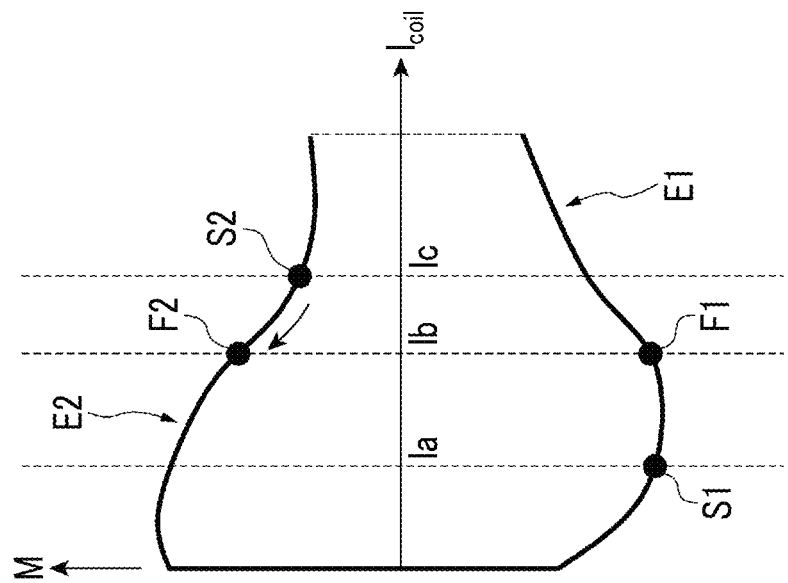
FIG. 5 is a diagram illustrating a relationship between the coil magnetization magnetic field and a current.

FIG. 5 schematically illustrates a region on the positive side of the horizontal axis of the graph of FIG. 4. However, the horizontal axis is replaced with the current value for the coil 30. For example, in a case where the current value of the coil 30 is directly changed from a start current value to a target current value (Ib), a value of the coil magnetization magnetic field differs depending on the magnitude relationship between the start current value and the target current value. That is, in a case where the start current value is "Ia" lower than "Ib", the value of the coil magnetization magnetic field transitions along the magnetization curve E1 on the negative side. In this case, the value of the coil magnetization magnetic field transitions along the magnetization curve E1 to be a value of a target point F1 from a value of a start point S1. In a case where the start current value is "Ic" higher than "Ib", the value of the coil magnetization magnetic field transitions along the magnetization curve E2 on the positive side. In this case, the value of the coil magnetization magnetic field transitions along the magnetization curve E2 to a value of a target point F2 from a value of a start point S2. In this manner, although the target current value finally reached is the same at "Ib", the value of the coil magnetization magnetic field at the target point F1 and the value of the coil magnetization magnetic field at the target point F2 are different from each other.

Therefore, in the control of changing the current value from a predetermined current value (hereinafter referred to as a start current value) to the target current value, the control unit 20 controls so that the value of the coil magnetization magnetic field at the target current value is the same regardless of the magnitude of the start current value. Immediately before reaching the target current value, the control unit 20 reduces the current value (demagnetization) to reach the target current value. In this case, the control unit 20 controls the current value so that the value of the coil magnetization magnetic field transitions along the magnetization curve E2 on the positive side immediately before reaching the target current value.

Figure 6A:
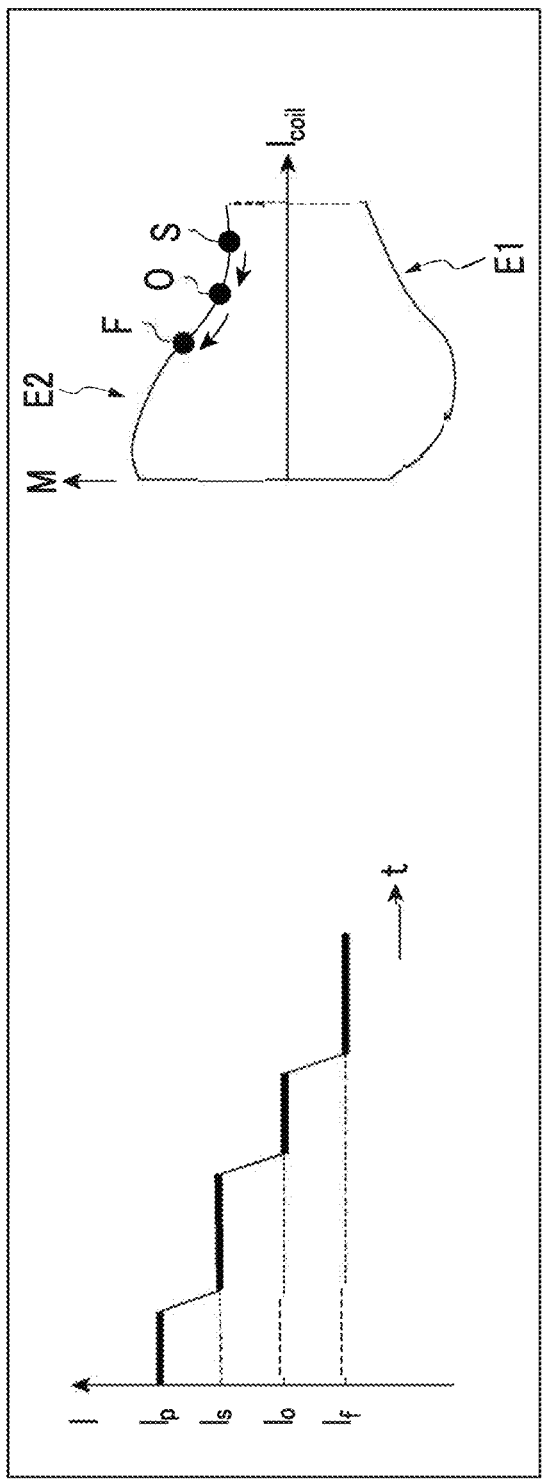
FIGS. 6A and 6B are graphs illustrating an aspect of a change in a current value and a change in the coil magnetization magnetic field.
Figure 6B:
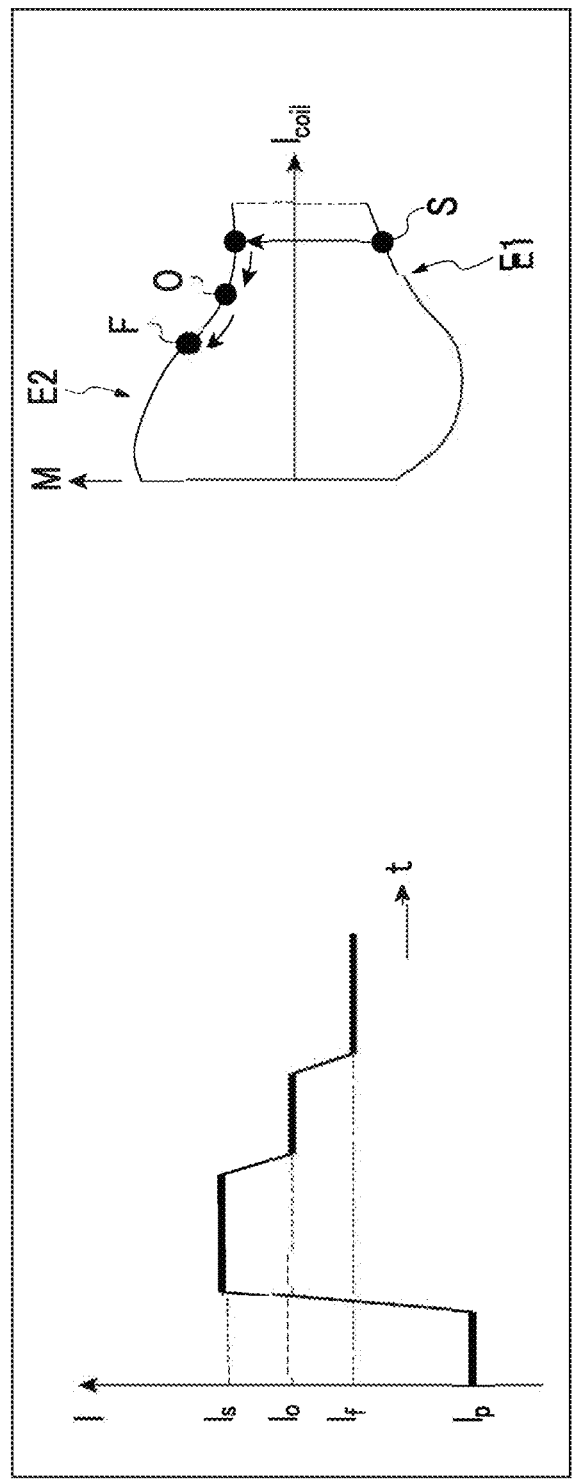

The control contents of the control unit 20 will be described with reference to FIGS. 6A to 7B. The graphs on the left side of FIGS. 6A and 6B are graphs illustrating the relationship between the transition of time and the transition of current value. The graphs on the right side of FIGS. 6A and 6B are graphs illustrating the relationship between the current value and the value of the coil magnetization magnetic field. The same applies to FIGS. 7A, 7B, and later. In the following description, "start current value Is" and "target current value If" are referred. In addition, a current value immediately before the start current value Is is referred to as an "immediately preceding current value Ip". Immediately before the target current value If, the current value for transitioning the value of the coil magnetization magnetic field along the positive magnetization curve E2 is referred to as a "format current value Io". In the graph illustrating the current value and the value of the coil magnetization magnetic field, the point corresponding to the start current value Is is referred to as a start point S, the point corresponding to the format current value Io is referred to as a format point O, and the point corresponding to the target current value If is referred to as a target point F.

FIGS. 6A to 7B illustrate the control contents of the control unit 20 in a case where the format current value Io is higher than the target current value If. In this case, regardless of how the value of the coil magnetization magnetic field transitions until reaching the format point O, when the value reaches the target point F from the format point O, the value transitions along the magnetization curve E2 on the positive side.

FIGS. 6A and 6B illustrate the control contents when the start current value Is is higher than the target current value If and the format current value Io. As illustrated in FIGS. 6A and 6B, in a case where the start current value Is is higher than the target current value If, the control unit 20 controls to lower the current value from the start current value Is to the target current value If.

FIG. 6A illustrates the control contents in a case where the immediately preceding current value Ip is higher than the start current value Is. In this case, since the control unit 20 lowers the current value in order to change from the immediately preceding current value Ip to the start current value Is (graph on the left side), the start point S exists on the magnetization curve E2 on the positive side (graph on the right side). The control unit 20 lowers the current value from the start current value Is to the format current value Io. As a result, the value of the coil magnetization magnetic field transitions from the start point S to the format point O along the magnetization curve E2 on the positive side. In addition, the control unit 20 lowers the current value from the format current value Io to the target current value If. As a result, the value of the coil magnetization magnetic field transitions from the format point O to the target point F along the magnetization curve E2 on the positive side.

FIG. 6B illustrates the control contents in a case where the immediately preceding current value Ip is lower than the start current value Is. In this case, since the control unit 20 raises the current value in order to change from the immediately preceding current value Ip to the start current value Is (graph on the left side), the start point S exists on the magnetization curve E1 on the negative side (graph on the right side). The control unit 20 raises the current value from the start current value Is to the format current value Io. In this case, the value of the coil magnetization magnetic field jumps from the start point S on the magnetization curve E1 on the negative side to the magnetization curve E2 on the positive side, and transitions to the format point O along the magnetization curve E2 on the positive side. In addition, the control unit 20 lowers the current value from the format current value Io to the target current value If. As a result, the value of the coil magnetization magnetic field transitions from the format point O to the target point F along the magnetization curve E2 on the positive side.

Figure 7A:
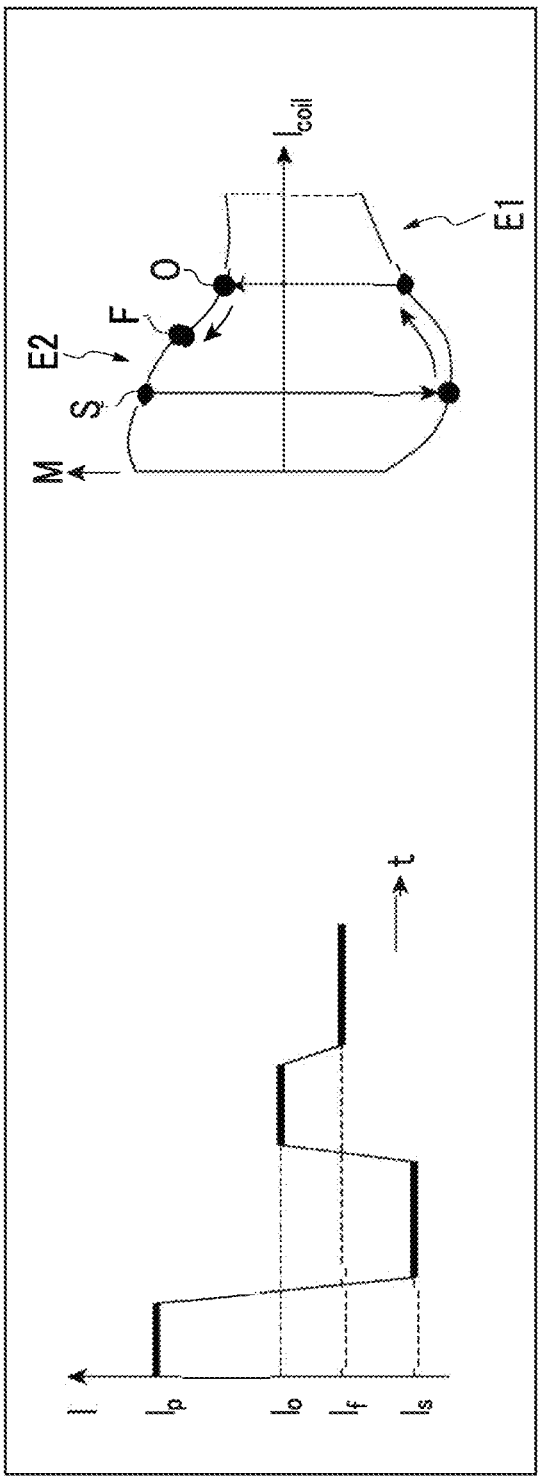
FIGS. 7A and 7B are graphs illustrating an aspect of a change in a current value and a change in the coil magnetization magnetic field.
Figure 7B:
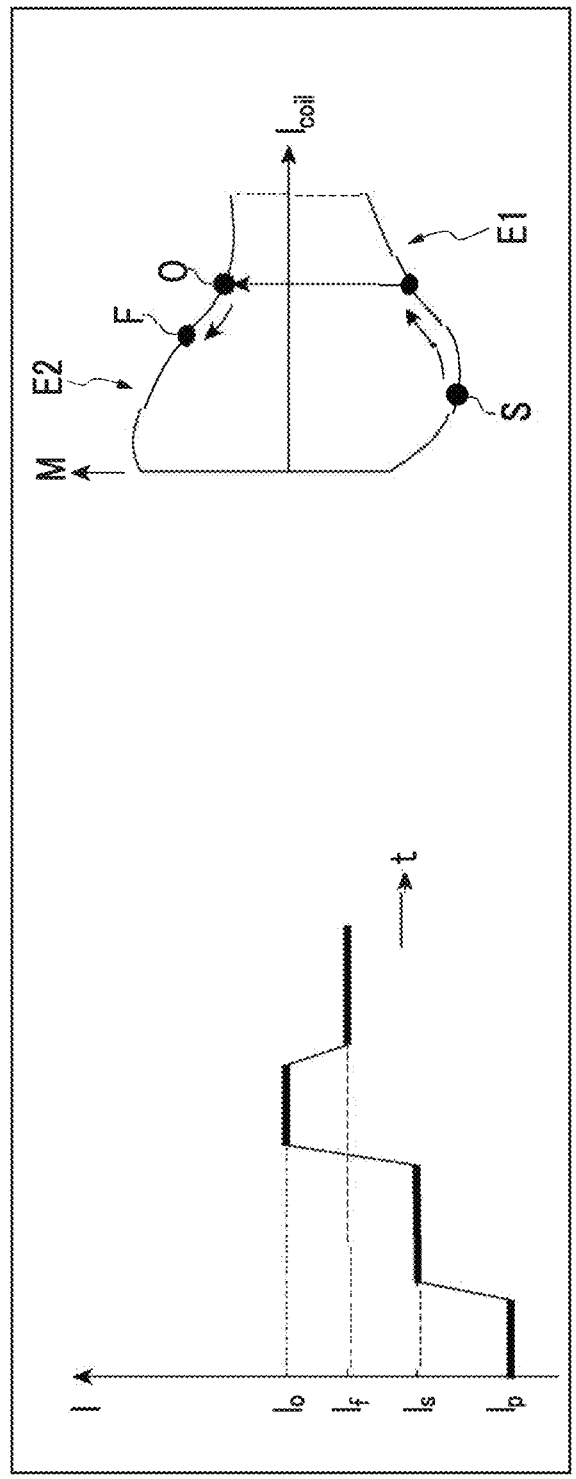

FIGS. 7A and 7B illustrate the control contents in which the start current value Is is equal to or lower than the target current value If and the format current value Io. As illustrated in FIGS. 7A and 7B, in a case where the start current value Is is equal to or lower than the target current value If, the control unit 20 controls to raise the current value from the start current value Is to the format current value Io higher than the target current value If, and then lower the current value to the target current value If.

FIG. 7A illustrates the control contents in a case where the immediately preceding current value Ip is higher than the start current value Is. In this case, since the control unit 20 lowers the current value in order to change from the immediately preceding current value Ip to the start current value Is (graph on the left side), the start point S exists on the magnetization curve E2 on the positive side (graph on the right side). The control unit 20 raises the current value from the start current value Is to the format current value Io. As a result, the value of the coil magnetization magnetic field jumps from the magnetization curve E2 on the positive side to the magnetization curve E1 on the negative side, transitions along the magnetization curve E1 on the negative side, and transitions to the position of the current value corresponding to the format point O. The control unit 20 lowers the current value from the format current value Io to the target current value If. As a result, the value of the coil magnetization magnetic field jumps from the magnetization curve E1 on the negative side to the magnetization curve E2 on the positive side, and transitions from the format point O to the target point F along the magnetization curve E2 on the positive side.

FIG. 7B illustrates the control contents in a case where the immediately preceding current value Ip is equal to or lower than the start current value Is. In this case, since the control unit 20 raises the current value in order to change from the immediately preceding current value Ip to the start current value Is (graph on the left side), the start point S exists on the magnetization curve E1 on the negative side (graph on the right side). The control unit 20 raises the current value from the start current value Is to the format current value Io. As a result, the value of the coil magnetization magnetic field transitions from the start point S along the magnetization curve E1 on the negative side, and transitions to the position of the current value corresponding to the format point O. The control unit 20 lowers the current value from the format current value Io to the target current value If. As a result, the value of the coil magnetization magnetic field jumps from the magnetization curve E1 on the negative side to the magnetization curve E2 on the positive side, and transitions from the format point O to the target point F along the magnetization curve E2 on the positive side.

The control contents by the control unit 20 are not limited to that illustrated in FIGS. 6A to 7B, and the control contents illustrated in FIGS. 8A to 9B may be adopted. FIGS. 8A to 9B illustrate the control contents of the control unit 20 in a case where the format current value Io is lower than the target current value If. In this case, regardless of how the value of the coil magnetization magnetic field transitions until reaching the format point O, when the value reaches the target point F from the format point O, the value transitions along the magnetization curve E1 on the negative side. That is, the control unit 20 controls the current value so that the value of the coil magnetization magnetic field transitions along the magnetization curve E1 on the negative side immediately before reaching the target current value.

Figure 8A:
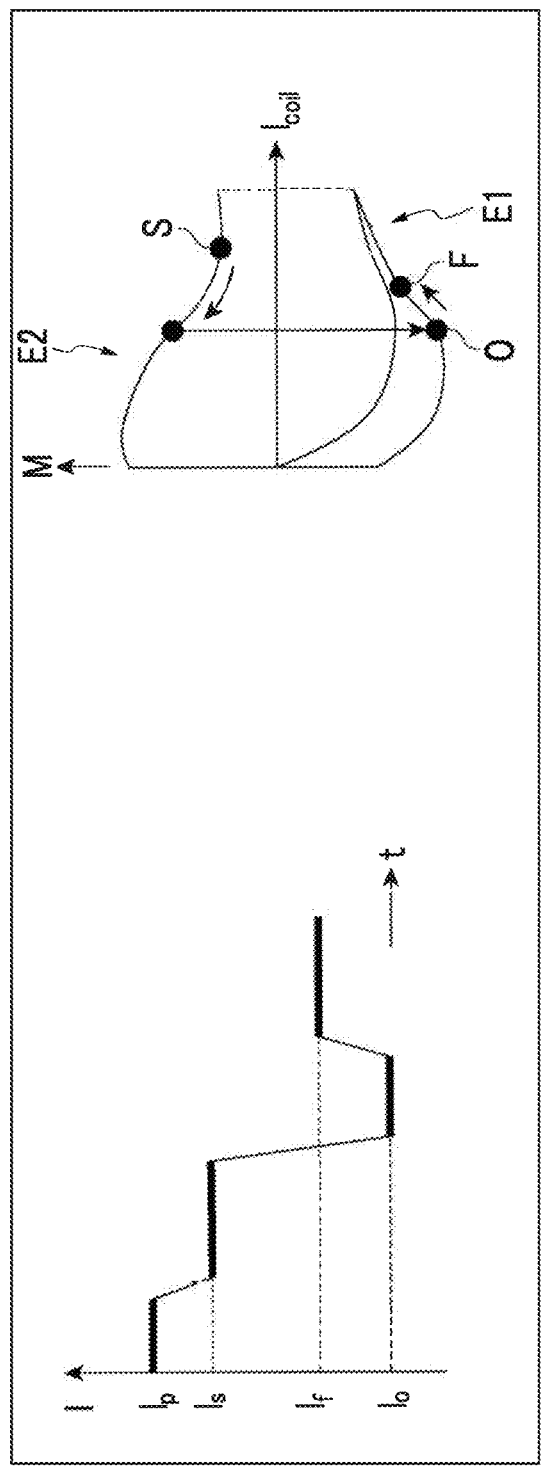
FIGS. 8A and 8B are graphs illustrating an aspect of a change in a current value and a change in the coil magnetization magnetic field.
Figure 8B:
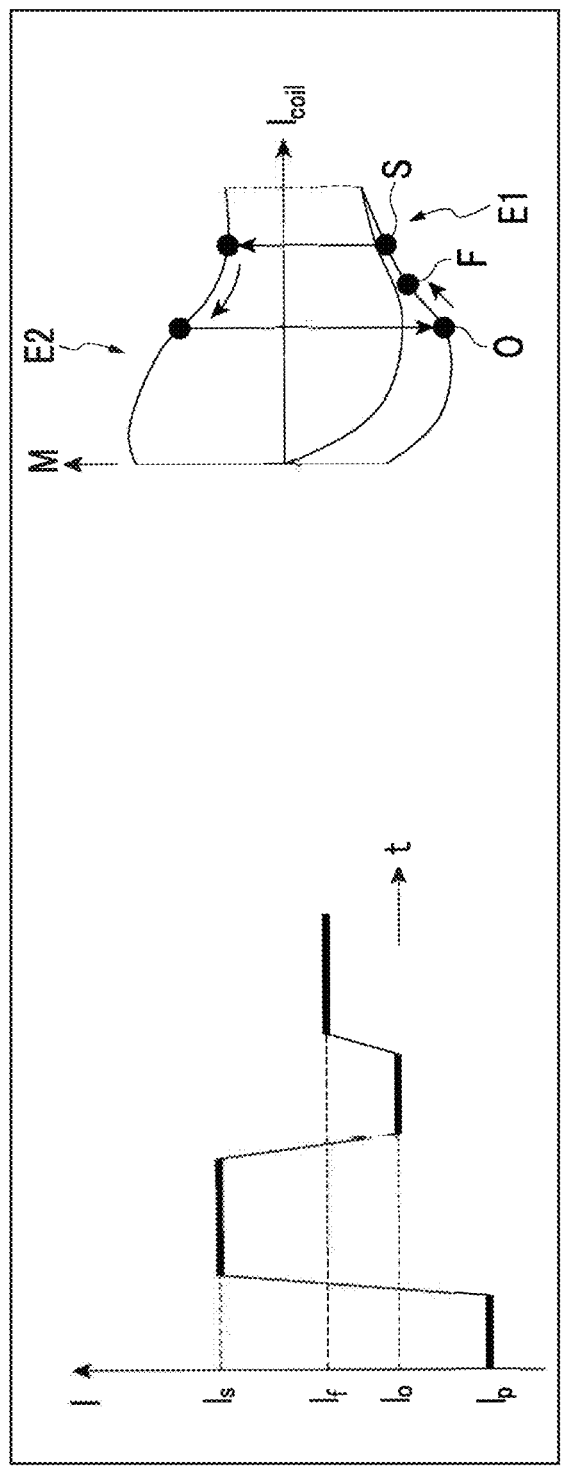

FIGS. 8A and 8B illustrate the control contents when the start current value Is is equal to or higher than the target current value If and the format current value Io. As illustrated in FIGS. 8A and 8B, the control unit 20 controls to lower the current value from the start current value Is to the format current value Io lower than the target current value If, and then raise the current value to the target current value If.

FIG. 8A illustrates the control contents in a case where the immediately preceding current value Ip is higher than the start current value Is. In this case, since the control unit 20 lowers the current value in order to change from the immediately preceding current value Ip to the start current value Is (graph on the left side), the start point S exists on the magnetization curve E2 on the positive side (graph on the right side). The control unit 20 lowers the current value from the start current value Is to the format current value Io. As a result, the value of the coil magnetization magnetic field transitions from the start point S to the position of the current value corresponding to the format point O along the magnetization curve E2 on the positive side. In addition, the control unit 20 lowers the current value from the format current value Io to the target current value If. As a result, the value of the coil magnetization magnetic field jumps from the magnetization curve E2 on the positive side to the magnetization curve E1 on the negative side, and transitions from the format point O to the target point F along the magnetization curve E1 on the negative side.

FIG. 8B illustrates the control contents in a case where the immediately preceding current value Ip is lower than the start current value Is. In this case, since the control unit 20 raises the current value in order to change from the immediately preceding current value Ip to the start current value Is (graph on the left side), the start point S exists on the magnetization curve E1 on the negative side (graph on the right side). The control unit 20 raises the current value from the start current value Is to the format current value Io. In this case, the value of the coil magnetization magnetic field jumps from the start point S on the magnetization curve E1 on the negative side to the magnetization curve E2 on the positive side, and transitions to the position of the current value corresponding to the format point O along the magnetization curve E2 on the positive side. In addition, the control unit 20 lowers the current value from the format current value Io to the target current value If. As a result, the value of the coil magnetization magnetic field jumps from the magnetization curve E2 on the positive side to the magnetization curve E1 on the negative side, and transitions from the format point O to the target point F along the magnetization curve E1 on the negative side.

Figure 9A:
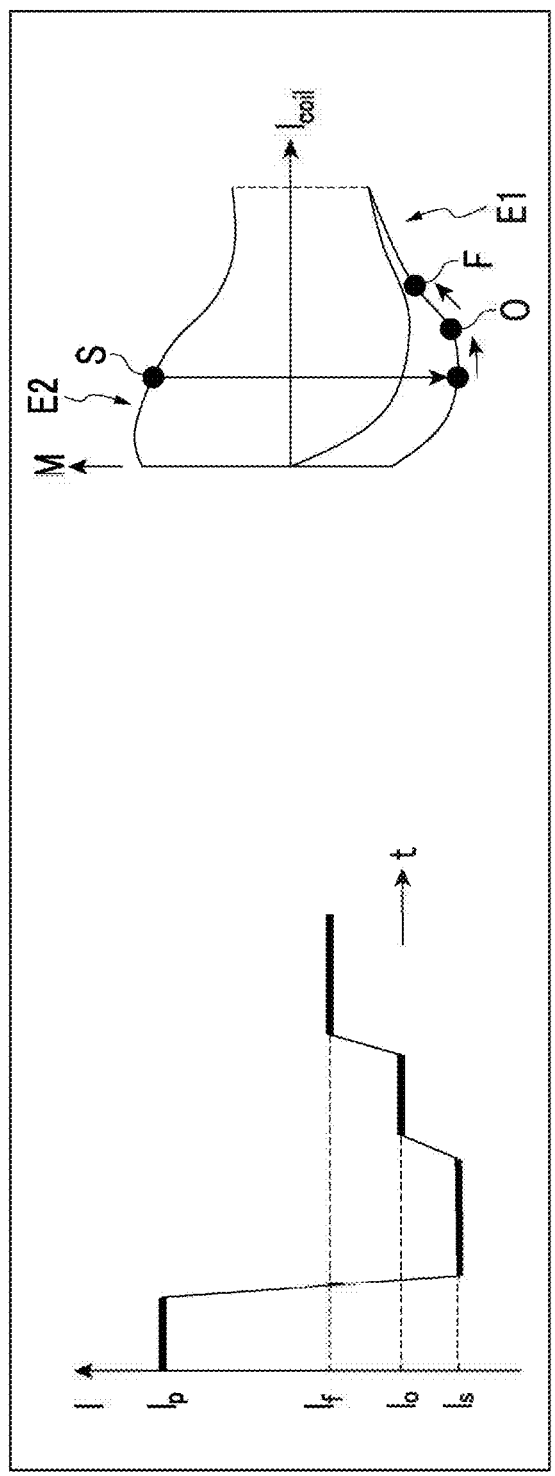
FIGS. 9A and 9B are graphs illustrating an aspect of a change in a current value and a change in the coil magnetization magnetic field.
Figure 9B:
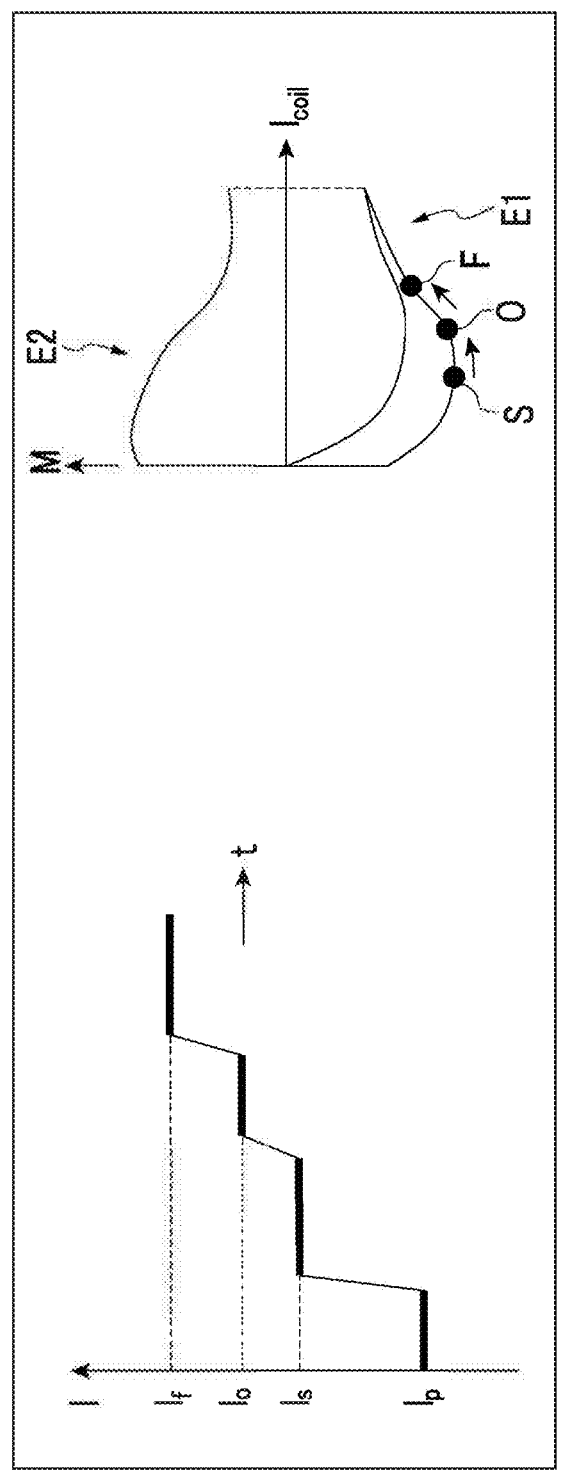

FIGS. 9A and 9B illustrate the control contents in a case where the start current value Is is lower than the target current value If and the format current value Io. As illustrated in FIGS. 9A and 9B, the control unit 20 controls to raise the current value from the start current value Is to the target current value If.

FIG. 9A illustrates the control contents in a case where the immediately preceding current value Ip is higher than the start current value Is. In this case, since the control unit 20 lowers the current value in order to change from the immediately preceding current value Ip to the start current value Is (graph on the left side), the start point S exists on the magnetization curve E2 on the positive side (graph on the right side). The control unit 20 raises the current value from the start current value Is to the format current value Io. As a result, the value of the coil magnetization magnetic field jumps from the magnetization curve E2 on the positive side to the magnetization curve E1 on the negative side, transitions along the magnetization curve E1 on the negative side, and transitions to the format point O. The control unit 20 raises the current value from the format current value Io to the target current value If. As a result, the value of the coil magnetization magnetic field transitions from the format point O to the target point F along the magnetization curve E1 on the negative side.

FIG. 9B illustrates the control contents in a case where the immediately preceding current value Ip is lower than the start current value Is. In this case, since the control unit 20 raises the current value in order to change from the immediately preceding current value Ip to the start current value Is (graph on the left side), the start point S exists on the magnetization curve E1 on the negative side (graph on the right side). The control unit 20 raises the current value from the start current value Is to the format current value Io. As a result, the value of the coil magnetization magnetic field transitions from the start point S along the magnetization curve E1 on the negative side and transitions to the format point O. The control unit 20 raises the current value from the format current value Io to the target current value If. As a result, the value of the coil magnetization magnetic field transitions from the format point O to the target point F along the magnetization curve E1 on the negative side.

Figure 10A:
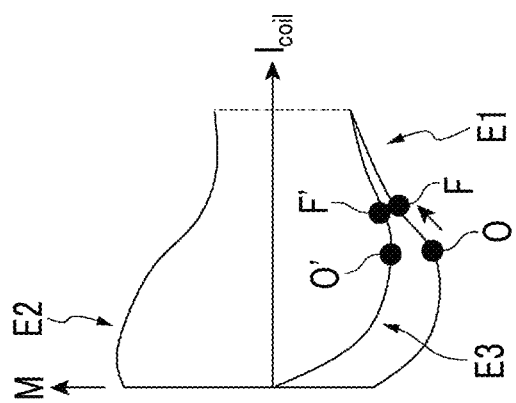
FIGS. 10A, 10B, and 10C are diagrams for describing control contents for eliminating a magnetization curve related to an initial magnetization process.

Here, as illustrated in FIG. 10A, the current sweep pattern has a magnetization curve E3 related to the initial magnetization process on the negative side of the coil magnetization magnetic field, in addition to the magnetization curve E1. The magnetization curve E3 related to the initial magnetization process is a magnetization curve in which the value of the coil magnetization magnetic field transitions in a case where a current value rising for the first time is flowed through the coil 30. For example, in a case where the format current value Io rises to the target current value If, when the value of the coil magnetization magnetic field transitions along the magnetization curve E1, the value transitions from the format point O to the target point F. However, when the value of the coil magnetization magnetic field transitions along the magnetization curve E3, the value transitions from a different format point O' to a different target point F'.

Figure 10B:
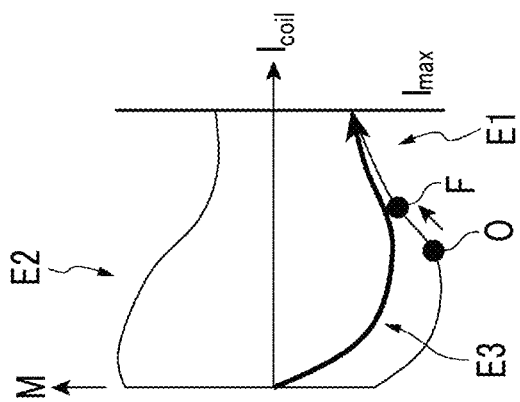
Figure 10C:
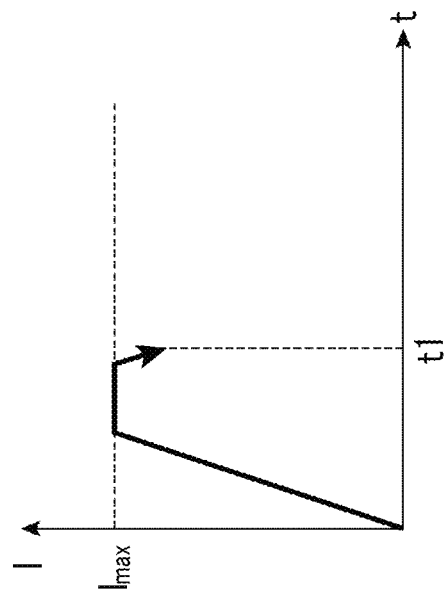

Here, when the value of the coil magnetization magnetic field passes through the magnetization curve E3 related to the initial magnetization process even once at a certain current value, the value transitions along the magnetization curve E1 from the next time onward. Therefore, as illustrated in FIG. 10C, in the sweep control of an initial current value, the control unit 20 performs the control to raise the current value to the maximum value Imax that can be obtained in the second and subsequent sweep controls. As a result, as illustrated in FIG. 10B, the value of the coil magnetization magnetic field can transition over the entire magnetization curve E3 related to the initial magnetization process by the initial sweep control. As a result, after the processing is performed (after the time t1 in FIG. 10C), when the processing illustrated in FIGS. 6A to 9B is performed, it is possible to control the value of the magnetization magnetic field to transition after the magnetization curves E1 and E2.

Next, the magnitude of the difference between the target current value If and the format current value Io will be described. The magnitude of the difference ΔI is set by the following equation (1). $\mu_0$ indicates the magnetic permeability of the vacuum, $J_c$ indicates the critical current value of the superconductor, and $r_f$ indicates the filament radius. $I_0$ is a predetermined energizing current value, and $B_m$ is the strength of the strongest magnetic flux density in the coil with respect to the energizing current value. Since the critical current value $J_c$ is defined by the temperature and the empirical magnetic field, $J_c$ has a range with respect to the operating temperature and the empirical magnetic field. For example, the value obtained by the equation (2) may be adopted as the value of α.

$$\Delta I = \alpha \mu_0 J_c r_f \tag{1}$$

$$\alpha = 2I_0/B_m \tag{2}$$

The control unit 20 keeps the current value of the coil 30 constant at the format current value Io for a predetermined time. The predetermined time to be constant is not particularly limited. For example, when the control unit 20 causes the current value to change from the start current value Is to the format current value Io, sufficient time may be secured for the value of the coil magnetization magnetic field to transition from the start point to the format point O. For example, the predetermined time to be constant may be set to approximately 30 to 600 seconds.

Figure 11B:
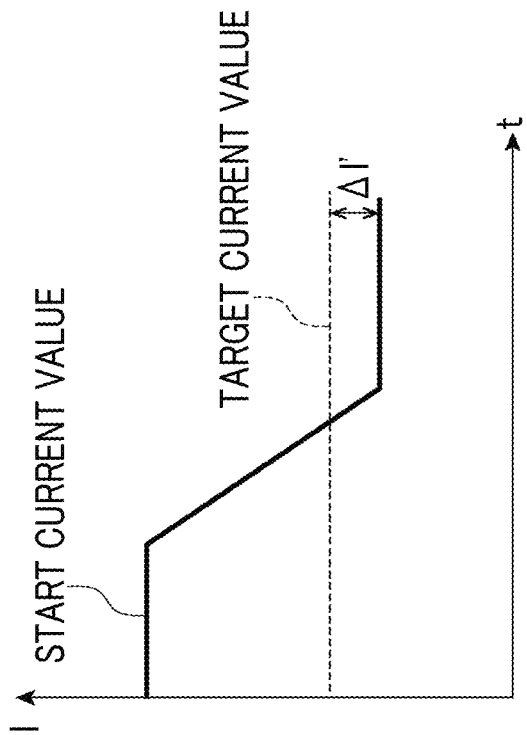
FIGS. 11A and 11B are graphs illustrating an aspect in which a current value deviated from a target current value by an estimated coil magnetization magnetic field flows through the coil.
Figure 11A:
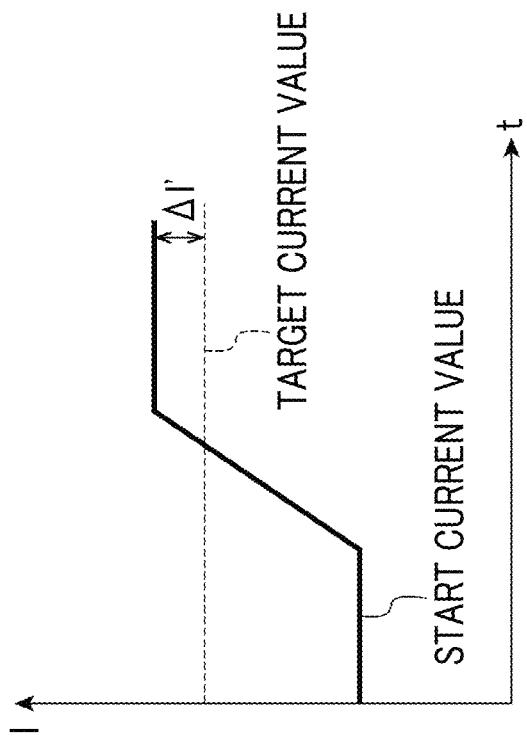

In the control contents illustrated in FIGS. 6A to 9B, the control unit 20 controls the current value, so that the value of the coil magnetization magnetic field transitions along the magnetization curve E1 on the negative side, or the value of the coil magnetization magnetic field transitions along the magnetization curve E2 on the positive side, immediately before reaching the target current value. Instead of this control, as illustrated in FIGS. 11A and 11B, in the control of changing the current value of the coil from the start current value to the target current value, the control unit 20 may estimate the coil magnetization magnetic field (magnetic field due to magnetization of coil 30 generated by change of current value) and flow a current value deviated from the target current value by the coil magnetization magnetic field through the coil 30.

Specifically, the control unit 20 causes the coil 30 to flow a current value deviated by an estimated value ΔI' with respect to the target current value I. For example, as illustrated in FIG. 11A, the control unit 20 causes a current value of "I+ΔI'" to flow through the coil 30. Alternatively, as illustrated in FIG. 11B, the control unit 20 causes a current value of "I−ΔI'" to flow through the coil 30. ΔI' is set by the equation (3). Each parameter is the same as the above-described equation (1). α needs to satisfy the expression (4). α may be obtained by calculating the sum of the magnetic fields of each unit volume for the magnetic field created at a predetermined point around the coil 30 by the magnetic moment per unit volume of the superconductor.

$$\Delta I' = \alpha \mu_0 I_c r_f \qquad (3)$$

$$2\frac{I_0}{B_m} \geq \alpha > \frac{I_0}{B_m} \qquad (4)$$

Next, the action or effect of the superconductive electromagnet 3 according to the present embodiment will be described.

As described above, in the superconductive electromagnet 3, the coil 30 uses the magnetic field MF as an external magnetic field, and magnetization is generated in the superconductor inside the coil 30 (coil magnetization magnetic field). As a result, the coil magnetization magnetic field is generated in the coil 30. Such a coil magnetization magnetic field cannot be ignored in a case where the demand for the absolute value of the magnetic field of the coil 30 is high. As illustrated in FIG. 1, the influence of the coil magnetization magnetic field as described above may cause a problem in the particle accelerator 1. Since there is a correlation between the coil magnetization magnetic field and the acceleration voltage frequency phase deviation, the coil magnetization magnetic field affects the acceleration of the particles. Therefore, the coil magnetization magnetic field depending on the current sweep pattern may cause a decrease in the acceleration efficiency of the particle accelerator 1. Since the particle accelerator 1 is required to have high accuracy, a superconductive electromagnet capable of reducing the influence of the coil magnetization magnetic field due to the coil magnetization magnetic field has been required.

Here, in the superconductive electromagnet 3, in a case where the current value of the coil 30 is changed from the start current value Is to the target current value If, there is a difference in the coil magnetization magnetic field due to the coil magnetization magnetic field even though the current value is the same as in a case where the target current value If is reached by lowering the current value and in a case where the target current value If is reached by raising the current value (refer to FIG. 5). On the other hand, as illustrated in FIGS. 6A to 7B, in a case where the start current value Is is higher than the target current value If, the control unit 20 controls to lower the current value from the start current value Is to the target current value If. In this case, the current value reaches the target current value If in a descending manner. In addition, in a case where the start current value Is is equal to or lower than the target current value If, the control unit 20 controls to raise the current value from the start current value Is to the format current value Io higher than the target current value If, and then lower the current value to the target current value If. In this case, the current value reaches the target current value If in a descending manner. In this manner, regardless of the value of the predetermined current value before the current value is changed, the current value reaches the target current value If in a descending manner. As a result, the coil magnetization magnetic field when the target current value If is reached can be kept in the same state regardless of the start current value Is before the current value is changed. Therefore, the influence of the coil magnetization magnetic field can be reduced.

In addition, as illustrated in FIGS. 8A to 9B, in a case where the start current value Is is lower than the target current value If, the control unit 20 controls to raise the current value from the start current value Is to the target current value If. In this case, the current value reaches the target current value If in an ascending manner. In addition, in a case where the predetermined current value is equal to or higher than the target current value If, the control unit 20 lowers the current value from the start current value Is to the format current value Io lower than the target current value If, and then raise the current value to the target current value If. In this case, the current value reaches the target current value If in an ascending manner. In this manner, regardless of the value of the start current value before the current value is changed, the current value reaches the target current value If in an ascending manner. As a result, the coil magnetization magnetic field when the target current value If is reached can be kept in the same state regardless of the start current value Is before the current value is changed. Therefore, the influence of the coil magnetization magnetic field can be reduced.

In addition, as illustrated in FIGS. 11A and 11B, the control unit 20 estimates the magnetic field due to the magnetization of the coil 30 generated by the change of the current value, and causes the current value deviated from the target current value by the coil magnetization magnetic field to flow through the coil 30.

In this case, the control unit 20 can control the current value flowing through the coil 30 by feedforward controlling the coil magnetization magnetic field in advance when changing from the start current value to the target current value. As a result, a magnetic field is formed around the coil 30 in an aspect in which the coil magnetization magnetic field is reduced. Therefore, the influence of the coil magnetization magnetic field can be reduced.

The control unit 20 may keep the current value of the coil 30 constant at the format current value Io for a predetermined time. In this case, sufficient time can be secured for the coil magnetization magnetic field to change.

In the initial sweep control of the current value, the control unit 20 may perform the control to raise the current value to the maximum current value Imax that can be obtained in the second and subsequent sweep controls. The value of the coil magnetization magnetic field can transition over the entire magnetization curve E3 related to the initial magnetization process by the initial sweep control. As a result, in the second and subsequent sweep controls, it is possible to suppress the change in the value of the coil magnetization magnetic field along the magnetization curve E3 related to the initial magnetization process.

The particle accelerator 1 according to the present embodiment is provided with the above-described superconductive electromagnet 3 and accelerates particles to generate a particle beam.

The particle beam therapy apparatus 100 according to the present embodiment is provided with the above-described particle accelerator 1 and performs treatment using the particle beam generated by the particle accelerator 1.

According to the particle accelerator 1, by accelerating charged particles using the above-described superconductive electromagnet 3, the influence of the coil magnetization magnetic field due to the coil magnetization magnetic field can be reduced, so that a particle accelerator with high acceleration efficiency can be obtained. In addition, according to the particle beam therapy apparatus 100, by using the particle accelerator 1 having high acceleration efficiency, it is possible to stably irradiate an irradiation target with a high beam current.

The present invention is not limited to the above-described embodiment.

For example, the superconductive electromagnet has been adopted in the particle accelerator, and the superconductive electromagnet may be adopted in a silicon single crystal pulling device or the like.

It should be understood that the invention is not limited to the above-described embodiment, but may be modified into various forms on the basis of the spirit of the invention. Additionally, the modifications are included in the scope of the invention.

What is claimed is:

1. A superconductive electromagnet that generates a magnetic field by flowing a current through a coil, the electromagnet comprising:
   a control unit that controls a current value of the coil, wherein the control unit
   performs a control to lower the current value from a predetermined current value of the coil to a target current value in a case where the predetermined current value is higher than the target current value, and
   performs a control to raise the current value from the predetermined current value to an intermediate current value, which is higher than the target current value, for changing the current value of the coil from the predetermined current value to the target current value, and then lower the current value to the target current value in a case where the predetermined current value is equal to or lower than the target current value.

2. The superconductive electromagnet according to claim 1, wherein
   the control unit keeps the current value of the coil constant at the intermediate current value for a predetermined time.

3. The superconductive electromagnet according to claim 1, wherein
   in an initial sweep control of a current value, the control unit performs a control to raise the current value to a maximum value that is obtainable in second and subsequent sweep controls.

4. A superconductive electromagnet that generates a magnetic field by flowing a current through a coil, the electromagnet comprising:
   a control unit that controls a current value of the coil, wherein the control unit
   performs a control to raise the current value from a predetermined current value of the coil to a target current value in a case where the predetermined current value is lower than the target current value, and
   performs a control to lower the current value from the predetermined current value to an intermediate current value, which is lower than the target current value, for changing the current value of the coil from the predetermined current value to the target current value, and then raise the current value to the target current value in a case where the predetermined current value is equal to or higher than the target current value.

5. A superconductive electromagnet that generates a magnetic field by flowing a current through a coil, the electromagnet comprising:
   a control unit that controls a current value of the coil, wherein
   the control unit estimates a magnetic field due to magnetization of the coil generated by a change of the current value, and causes a current value deviated from a target current value by the magnetic field due to the magnetization of the coil to flow through the coil.

6. A particle accelerator comprising:
   a magnetic pole;
   a coil disposed around the magnetic pole;
   a vacuum chamber that accommodates the coil; and
   a control unit that controls a current value of the coil, wherein the control unit
   accelerates a charged particle to generate a particle beam by performing a control to lower a current value from a predetermined current value of the coil to a target current value in a case where the predetermined current value is higher than the target current value, and
   performs a control to raise a current value from the predetermined current value to an intermediate current value, which is higher than the target current value, for changing the current value of the coil from the predetermined current value to the target current value, and then lower the current value to the target current value in a case where the predetermined current value is equal to or lower than the target current value, by the control unit.

7. A particle beam therapy apparatus comprising:
   a particle accelerator that includes
     a magnetic pole,
     a coil disposed around the magnetic pole,
     a vacuum chamber that accommodates the coil, and
     a control unit that controls a current value of the coil, wherein the control unit
   accelerates a charged particle to generate a particle beam by performing a control to lower a current value from a predetermined current value of the coil to a target current value in a case where the predetermined current value is higher than the target current value, and
   performs a control to raise a current value from the predetermined current value to an intermediate current value, which is higher than the target current value, for changing the current value of the coil from the predetermined current value to the target current value, and then lower the current value to the target current value in a case where the predetermined current value is equal to or lower than the target current value, by the control unit, and
   the apparatus performs treatment using the particle beam generated by the particle accelerator.

* * * * *